United States Patent [19]

Mayer

[11] Patent Number: 5,630,840
[45] Date of Patent: May 20, 1997

[54] CLAD COMPOSITE STENT

[75] Inventor: David W. Mayer, Bloomington, Minn.

[73] Assignee: Schneider (USA) Inc, Plymouth, Minn.

[21] Appl. No.: 483,334

[22] Filed: Jun. 7, 1995

Related U.S. Application Data

[60] Division of Ser. No. 239,595, May 9, 1994, which is a continuation-in-part of Ser. No. 6,216, Jan. 19, 1993, abandoned.

[51] Int. Cl.⁶ ................................................. A61F 2/06
[52] U.S. Cl. .................... 623/1; 623/11; 623/12; 606/194; 606/195; 606/198
[58] Field of Search .................... 623/1, 11, 12; 606/194, 195, 198

[56] References Cited

U.S. PATENT DOCUMENTS

| | | |
|---|---|---|
| 2,524,661 | 10/1950 | Harder et al. |
| 3,466,166 | 9/1969 | Levinstein et al. |
| 3,562,024 | 2/1971 | Smith et al. |
| 4,023,557 | 5/1977 | Thorne et al. |
| 4,281,419 | 8/1981 | Treace |
| 4,465,481 | 8/1984 | Blake |
| 4,600,446 | 7/1986 | Torisaka et al. |
| 4,655,771 | 4/1987 | Wallsten ............ 623/1 |
| 4,719,916 | 1/1988 | Ravo |
| 4,731,084 | 3/1988 | Dunn et al. |
| 4,830,262 | 5/1989 | Ishibe |
| 4,848,348 | 7/1989 | Craighead |
| 4,883,486 | 11/1989 | Kapadia et al. |
| 4,950,227 | 8/1990 | Savin et al. |
| 5,001,825 | 3/1991 | Halpern |
| 5,003,987 | 4/1991 | Grinwald |
| 5,003,989 | 4/1991 | Taylor et al. |
| 5,015,253 | 5/1991 | MacGregor |
| 5,024,232 | 6/1991 | Smid et al. |

(List continued on next page.)

FOREIGN PATENT DOCUMENTS

| | | |
|---|---|---|
| 547739A1 | 6/1993 | European Pat. Off. |
| 556940A1 | 8/1993 | European Pat. Off. |
| 593136A1 | 4/1994 | European Pat. Off. |
| 067929 | 12/1982 | Germany |
| 0259541 | 10/1989 | Japan |

OTHER PUBLICATIONS

WO 93/19803 "Medical Wire"; Oct. 1993; Heath et al.
WO 93/19804 "Tubular Medical Endoprostheses"; Oct. 1993; Heath et al.

(List continued on next page.)

*Primary Examiner*—David Isabella
*Assistant Examiner*—John M. Black
*Attorney, Agent, or Firm*—Haugen and Nikolai, P.A.

[57] ABSTRACT

A body compatible stent is formed of multiple filaments arranged in at least two sets of oppositely directed helical windings interwoven with one another in a braided configuration. Each of the filaments is a composite including a central core and a case surrounding the core. In the more preferred version, the core is formed of a radiopaque and relatively ductile material, e.g. tantalum or platinum. The outer case is formed of a relatively resilient material, e.g. a cobalt/chromium based alloy. Favorable mechanical characteristics of the stent are determined by the case, while the core enables in vivo imaging of the stent. The composite filaments are formed by a drawn filled tubing process in which the core is inserted into a tubular case of a diameter substantially more than the intended final filament diameter. The composite filament is cold-worked in several steps to reduce its diameter, and annealed between successive cold-working steps. After the final cold working step, the composite filament is formed into the desired shape and age hardened. The composite filaments employ an intermediate barrier layer between the case and core, formed for example of tantalum, niobium or platinum. To improve compatibility, a biocompatible cover layer can surround the case. An alternative composite filament features, and a radiopaque case surrounding a structural core.

22 Claims, 2 Drawing Sheets

U.S. PATENT DOCUMENTS

| | | |
|---|---|---|
| 5,047,050 | 9/1991 | Arpesani . |
| 5,069,226 | 12/1991 | Yamauchi et al. . |
| 5,092,877 | 3/1992 | Pinchuk . |
| 5,104,404 | 4/1992 | Wolff . |
| 5,139,480 | 8/1992 | Hickle et al. . |
| 5,201,901 | 4/1993 | Harada et al. . |
| 5,207,706 | 5/1993 | Menaker . |
| 5,213,111 | 5/1993 | Cook et al. ............... 128/772 |
| 5,217,483 | 6/1993 | Tower . |
| 5,256,764 | 10/1993 | Tang et al. ............... 528/370 |
| 5,320,100 | 6/1994 | Herweck et al. . |
| 5,360,442 | 11/1994 | Dahl et al. . |
| 5,374,261 | 12/1994 | Yoon . |
| 5,382,259 | 1/1995 | Phelps et al. . |
| 5,389,106 | 2/1995 | Tower . |
| 5,514,154 | 5/1996 | Lau et al. ............... 606/195 |

OTHER PUBLICATIONS

WO 92/13483 "Multifilar Coil Guide Wire"; Aug. 1992; Fleischhacker, et al.

WO 94/16646 "Clad Composite Stent"; Aug. 1994; Mayer.

PCT/US93/11262, Search Report; Nov. 1993; Schneider (USA) Inc.

"DFT—Drawn Filled Tubing".

"Intravasclar Stents to Prevent Occlusion and Restenosis After Transluminal Angioplasty", The New England Journal of Medicine, Sigwart et al, vol. 316, Mar. 19, 1987, No. 12.

"Strengthening mechanisms in Elgiloy", Journal of Materials Science, Assefpour–Dezfuly et al; Nov. 1983; pp. 2815–2836.

PCT/IB 95/00253, Search Report, Nov. 1995, Schneider (USA) Inc.

1991 Annual Book of ASTM Standards, vol. 13.01 Medical Devices.

Search Report in PCT/US93/11262 Info. Sheet "Drawn Filled Tubing" Published by Fort Wayne Metals Research Products.

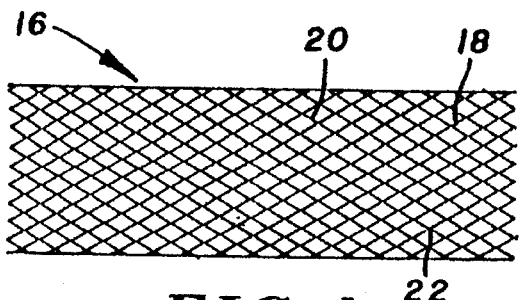
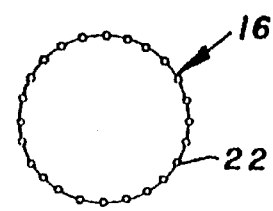
FIG.1  FIG.2
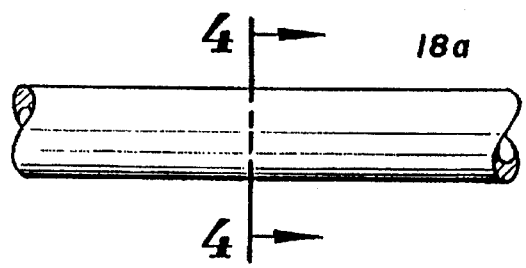
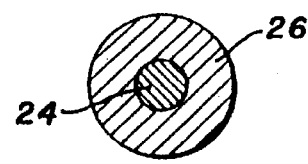
FIG.3  FIG.4
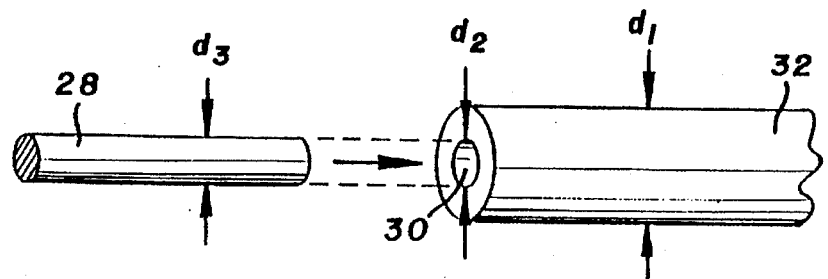
FIG.5
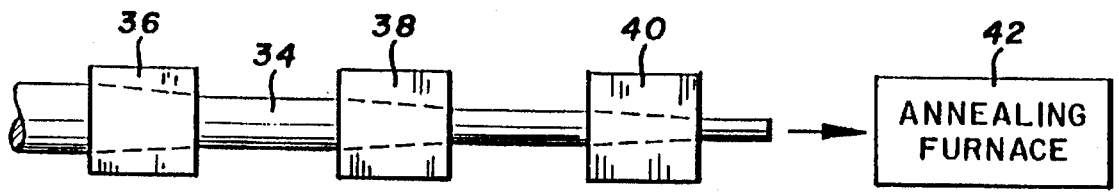
FIG.6
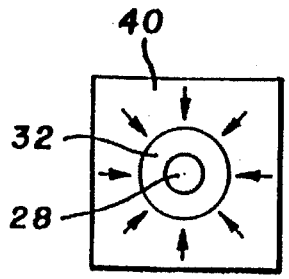
FIG.7

CLAD COMPOSITE STENT

This is a divisional of application Ser. No. 08/239,595, filed May 9, 1994, which is a continuation-in-part of application Ser. No. 08,006,216, filed Jan. 19, 1993, abandoned.

BACKGROUND OF THE INVENTION

The present invention relates to body implantable medical devices, and more particularly to stents and other prostheses configured for high radio-opacity as well as favorable mechanical characteristics.

Recently several prostheses, typically of lattice work or open frame construction, have been developed for a variety of medical applications, e.g. intravascular stents for treating stenosis, prostheses for maintaining openings in the urinary tracts, biliary prostheses, esophageal stents, renal stents, and vena cava filters to counter thrombosis. One particularly well accepted device is a self-expanding mesh stent disclosed in U.S. Pat. No. 4,655,771 (Wallsten). The stent is a flexible tubular braided structure formed of helically wound thread elements. The thread elements can be constructed of a biocompatible plastic or metal, e.g. certain stainless steels, polypropylene, polyesters and polyurethanes.

Alternatively, stents and other prostheses can be expandable by plastic deformation, usually by expanding a dilation balloon surrounded by the prosthesis. For example, U.S. Pat. No. 4,733,665 (Palmaz) discloses an intraluminal graft constructed of stainless steel strands, either woven or welded at their intersections with silver. U.S. Pat. No. 4,886,062 (Wiktor) features a balloon expandable stent constructed of stainless steel, a copper alloy, titanium, or gold.

Regardless of whether the prosthesis is self-expanding or plastically expanded, accurate placement of the prosthesis is critical to its effective performance. Accordingly, there is a need to visually perceive the prosthesis as it is being placed within a blood vessel or other body cavity. Further, it is advantageous and sometimes necessary to visually locate and inspect a previously deployed prosthesis.

Fluoroscopy is the prevailing technique for such visualization, and it requires radio-opacity in the materials to be imaged. The preferred structural materials for prosthesis construction, e.g. stainless steels and cobalt-based alloys, are not highly radiopaque. Consequently, prostheses constructed of these materials do not lend themselves well to fluoroscopic imaging.

Several techniques have been proposed, in apparent recognition of this difficulty. For example, U.S. Pat. No. 4,681,110 (Wiktor) discloses a self-expanding blood vessel liner formed of woven plastic strands, radially compressed for delivery within a tube. A metal ring around the tube is radiopaque. Similarly, U.S. Pat. No. 4,830,003 (Wolff) discusses confining a radially self-expanding stent within a delivery tube, and providing radiopaque markers on the delivery tube. This approach facilitates imaging only during deployment and initial placement.

To permit fluoroscopic imaging after placement, the stent itself must be radiopaque. The Wolff patent suggests that the stent can be formed of platinum or a platinum-iridium alloy for substantially greater radio-opacity. Such stent, however, lacks the required elasticity, and would exhibit poor resistance to fatigue. The Wiktor '110 patent teaches the attachment of metal staples to its blood vessel liner, to enhance radio-opacity. However, for many applications (e.g. in blood vessels), the stent is so small that such staples either would be too small to provide useful fluoroscopic imaging, or would adversely affect the efficiency and safety of deploying the stent or other prosthesis. This Wiktor patent also suggests infusing its plastic strands with a suitable filler, e.g. gold or barium sulfate, to enhance radio-opacity. Wiktor provides no teaching as to how this might be done. Further, given the small size of prostheses intended for blood vessel placement, this technique is unlikely to materially enhance radio-opacity, due to an insufficient amount and density of the gold or barium sulfate.

Therefore, it is an object of the present invention to provide a stent or other prosthesis with substantially enhanced radio-opacity, without any substantial reduction in the favorable mechanical properties of the prosthesis.

Another object is to provide a resilient body insertable composite filament having a high degree of radio-opacity and favorable structural characteristics, even for stents employing relatively small diameter filaments.

A further object is to provide a process for manufacturing a composite filament consisting essentially of a structural material for imparting desired mechanical characteristics, in combination with a radiopaque material to substantially enhance fluoroscopic imaging of the filament.

Yet another object is to provide a case composite prosthesis in which a highly radiopaque material and a structural material cooperate to provide mechanical stability and enhanced fluoroscopic imaging, and further are selectively matched for compatibility as to their crystalline structure, coefficients of thermal expansion, and annealing temperatures.

SUMMARY OF THE INVENTION

To achieve these and other objects, there is provided a process for manufacturing a resilient body insertable composite filament. The process includes the following steps:

a. providing an elongate cylindrical core substantially uniform in lateral cross-section and having a core diameter, and an elongate tubular case or shell substantially uniform in lateral cross-section and having a case inside diameter, wherein one of the core and case is formed of a radiopaque material and the other is formed of a resilient material having a yield strength (0.2% offset) of at least 100,000 psi, wherein the core diameter is less than the interior diameter of the case, and the lateral cross-sectional area of the core and case is at most ten times the lateral cross-sectional area of the core;

b. inserting the core into the case to form an elongate composite filament in which the case surrounds the core;

c. cold-working the composite filament to reduce the lateral cross-sectional area of the composite filament by at least 15%, whereby the composite filament has a selected diameter less than an initial outside diameter of composite filament before cold-working;

d. annealing the composite filament after cold-working, to substantially remove strain hardening and other stresses induced by the cold-working step;

e. mechanically forming the annealed composite filament into a predetermined shape; and f. after the cold-working and annealing steps, and while maintaining the composite filament in the predetermined shape, age hardening the composite filament.

In one preferred version of the process, the radiopaque material has a linear attenuation coefficient, at 100 KeV, of at least 25 $cm^{-1}$. The radiopaque material forms the core, and is at least as ductile as the case. The outside diameter of the composite filament, before cold-working, preferably is at most about six millimeters (about 0.25 inches). The cold-working step can include drawing the composite filament serially through several dies, with each die plastically deforming the composite filament to reduce the outside diameter. Whenever a stage including one or more cold-working dies has reduced the cross-sectional area by at least 25%, an annealing step should be performed before any further cold-working.

During each annealing step, the composite filament is heated to a temperature in the range of about 1700°–2300° F. more preferably 1950°–2150° F. for a period depending on the filament diameter, typically in the range of several seconds to several minutes. The core material and cladding (case) materials preferably are selected to have overlapping annealing temperature ranges, and similar coefficients of thermal expansion. The core and case materials further can be selectively matched as to their crystalline structure and metallurgical compatibility.

In an alternative version of the process, the initial outside diameter of the composite structure (billet) typically is at least fifty millimeters (about two inches) in diameter. Then, before cold-working, the composite filament is subjected to temperatures in the annealing range while the outside diameter is substantially reduced, either by swaging or by pulltrusion, in successive increments until the outside diameter is at most about 6 millimeters (0.25 inches). The resulting filament is processed as before, in alternative cold-working and annealing stages.

Further according to the process, the composite filament can be severed into a plurality of strands. Then, the strands are arranged in two oppositely directed sets of parallel helical windings about a cylindrical form, with the strands intertwined in a braided configuration to form multiple intersections. Then, while the strands are maintained in a predetermined uniform tension, they are heated to a temperature in the range of about 700°–1200° F., more preferably 900°–1000° F., for a time sufficient to age harden the helical windings.

The result of this process is a resilient, body implantable prosthesis. The prosthesis has a plurality of resilient strands, helically wound in two oppositely directed sets of spaced apart and parallel strands, interwoven with one another in a braided configuration. Each of the strands includes an elongate core and an elongate tubular case surrounding the core. A cross-sectional area of the core is at least ten percent of the cross-sectional area of the strand. The core is constructed of a first material having a linear attenuation coefficient of at least 25 cm$^{-1}$ at 100 KeV. The case is constructed of a resilient second material, less ductile than the first material.

More generally, the process can be employed to form a body compatible device comprising an elongate filament substantially uniform in lateral cross-section over its length and including an elongate cylindrical core and an elongate tubular case surrounding the core. One of the core and case is constructed of a first material having a yield strength (0.2% offset) of at least twice that of the second material. The other of the core and case is constructed of a second material being radiopaque and at least as ductile as the first material.

In a highly preferred version of the invention, the core is constructed of tantalum for radio-opacity, and the case is constructed of a cobalt-based alloy, e.g. as available under the brand names "Elgiloy", "Phynox" and "MP35N". The "Elgiloy" and "Phynox" alloys contain cobalt, chromium, nickel, and molybdenum, along with iron. Either of these alloys is well matched with tantalum, in terms of overlapping annealing temperature ranges, coefficients of thermal expansion and crystalline structure. The tantalum core and alloy case can be contiguous with one another, with virtually no formation of intermetallics.

When otherwise compatible core and case materials present the risk of intermetallic formation, an intermediate layer, e.g. of tantalum, niobium, or platinum, can be formed between the core and the case to provide a barrier against intermetallic formation. Further, if the case itself is not sufficiently biocompatible, a biocompatible coating or film can surround the case. Tantalum, platinum, iridium, titanium and their alloys or stainless steels can be used for this purpose.

While disclosed herein in connection with a radially self-expanding stent, the composite filaments can be employed in constructing other implantable medical devices, e.g. vena cava filters, blood filters and thrombosis coils. Thus, in accordance with the present invention there is provided a resilient, body compatible prosthesis which, despite being sufficiently small for placement within blood vessels and similarly sized body cavities, has sufficient radio-opacity for fluoroscopic imaging based on the prosthesis materials themselves.

IN THE DRAWINGS

For a further understanding of the above and other features and advantages, reference is made to the following detailed description and to the drawings, in which:

FIG. 1 is a side elevation of a self-expanding stent constructed according to the present invention;

FIG. 2 is an end elevational view of the stent;

FIG. 3 is an enlarged partial view of one of the composite filaments forming the stent;

FIG. 4 is an enlarged sectional view taken along the line 4—4 in FIG. 3;

Figure 10:
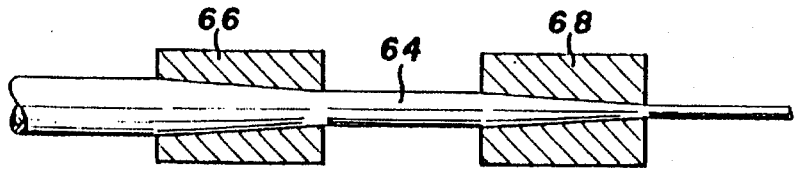
Figure 11:
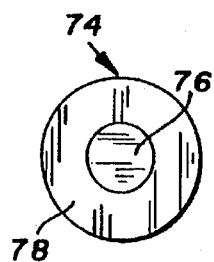
Figure 12:
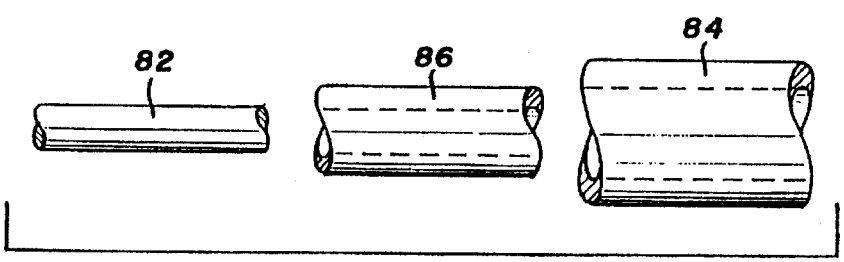
Figure 13:
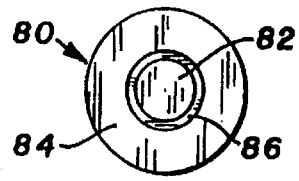
Figure 14:
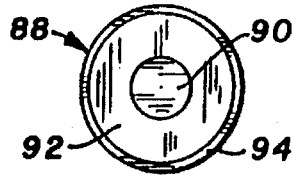

FIGS. 5–9 schematically illustrate a process for manufacturing the stent;

FIG. 10 schematically illustrates a swaging step of an alternative process for manufacturing the stent;

FIG. 11 is an end elevational view of an alternative embodiment filament;

FIG. 12 is an elevational view of several components of an alternative composite filament constructed according to the present invention;

FIG. 13 is an end elevational view of the composite filament formed by the components shown in FIG. 12; and FIG. 14 is an end elevational view of another alternative embodiment composite filament.

DETAILED DESCRIPTION OF THE PREFERRED EMBODIMENT

Turning now to the drawings, there is shown in FIGS. 1 and 2 a body implantable prosthesis 16, frequently referred to as a stent. Stent 16 is of open mesh or weave construction, consisting of two sets of oppositely directed, parallel and spaced apart helically wound strands or filaments indicated at 18 and 20, respectively. The sets of strands are interwoven in an over and under braided configuration to form multiple intersections, one of which is indicated at 22.

Stent 16 is illustrated in its relaxed state, i.e. in the configuration it assumes when subject to no external stresses. The filaments or strands of stent 16 are resilient, permitting a radial compression of the stent into a reduced-radius, extended-length configuration suitable for transluminal delivery of the stent to the intended placement site. As a typical example, stent 16 can have a diameter of about ten millimeters in the relaxed state, and is elastically compressed to a diameter of about 2 millimeters (0.08 inches) and an axial length of about twice the axial length of the relaxed stent. However, different applications call for different diameters. Further, it is well known to predetermine the degree of axial elongation for a given radial compression, by selectively controlling the angle between the oppositely directed helical strands.

Inelastic open-weave prostheses, expandable for example by dilation balloons, provide an alternative to resilient prostheses. Resilient or self-expanding prostheses often are preferred, as they can be deployed without dilation balloons or other stent expanding means. Self-expanding stents can be preselected according to the diameter of the blood vessel or other intended fixation site. While their deployment requires skill in stent positioning, such deployment does not require the additional skill of carefully dilating the balloon to plastically expand the prosthesis to the appropriate diameter. Further, the self-expanding stent remains at least slightly elastically compressed after fixation, and thus has a restoring force which facilitates acute fixation. By contrast, a plastically expanded stent must rely on the restoring force of deformed tissue, or on hooks, barbs, or other independent fixation elements.

Accordingly, materials forming the strands for filaments must be strong and resilient, biocompatible, and resistant to fatigue and corrosion. Vascular applications require hemocompatibility as well. Several materials meet these needs, including stainless "spring" steels, and certain cobalt-based alloys: more particularly two alloys including cobalt, chromium, iron, nickel and molybdenum sold under the brand names "Elgiloy" (available from Carpenter Technology Corporation of Reading, Pa.) and "Phynox" (available from Metal Imphy of Imphy, France), respectively. Another suitable cobalt-chromium alloy is available under the brand name "MP35N" from Carpenter Technology Corporation of Reading, Pa. and Latrobe Steel company, Latrobe, Pa.

Further, it is advantageous to form a prosthesis with substantial open space to promote embedding of the stent into tissue, and fibrotic growth through the stent wall to enhance long-term fixation. A more open construction also enables substantial radial compression of the prosthesis for deployment. In a typical construction suitable for transluminal implantation, the filaments can have a diameter of about 0.1 millimeter (0.004 inches), with adjacent parallel filaments spaced apart from one another by about 1-2 millimeters (0.04-0.08 inches) when the stent is in the relaxed state.

Fluoroscopic imaging of a conventional open weave prosthesis is extremely difficult. Due to their minute diameters and the materials involved, the filaments exhibit a relatively poor contrast to body tissue for fluoroscopic imaging purposes. The filaments also require a high degree of spatial resolution in the imaging equipment involved. Thus, a stent recognizable on X-ray film may not be distinguishable for real time imaging, due to the relatively poor spatial resolution of the video monitor as compared to X-ray film.

According to the present invention, however, prosthesis 16 is substantially more amenable to fluoroscopic imaging, due to the construction of strands 18 and 20. In particular, the strands cooperate to present a sufficiently radiopaque mass at the tangents of device 16 (parallel to the X-rays) for satisfactory real time imaging. As seen in FIGS. 3 and 4, a filament 18a of he prosthesis is of composite construction, with a radiopaque core 24 surrounded by and concentric with an annular resilient case 26. Core 24 is highly absorptive of X-rays, preferably having a linear attenuation coefficient of at least 25 (and more preferably at least 40) $cm^{-1}$ at 100 KeV. Materials with relatively high atomic numbers and densities tend to have the necessary attenuation coefficients. More particularly, it has been found that materials with an atomic number (element) or "effective" atomic number (based on a weighted average of elements in alloys or compounds) of at least fifty, and densities of at least 0.5 pounds per cubic inch, exhibit the required ability to absorb X-rays. Finally, core 24 is preferably a ductile material so that it readily conforms to the shape of the case.

By contrast, case 26 is formed of a highly resilient material, preferably with a yield strength (0.2% offset) of at least 150,000 psi. More preferably, the yield strength is at least 300,000 psi. Consequently, the mechanical behavior of composite filament 18a in terms of elastic deformation in response to external stresses is, essentially, the behavior of case 26.

In addition to individual characteristics of the core and case, it is desirable to selectively match core and case materials based on certain common characteristics. The core and case materials should have the same or substantially the same linear coefficients of thermal expansion. Similarity of core and case materials in their crystalline structure is also an advantage. Finally, the core and case materials should have an overlap in their annealing temperature ranges, to facilitate manufacture of the filaments according to the process to be explained.

In a highly preferred embodiment, core 24 is formed of tantalum, and case 26 is formed of a cobalt-based alloy, more particularly Elgiloy (brand) alloy. Tantalum is a ductile metal having an atomic number of 73 and a density of about 0.6 pounds per cubic inch. Its linear attenuation coefficient, at 100 KeV, is 69.7 $cm^{-1}$.

The Elgiloy alloy includes principally cobalt and chromium, and has an effective atomic number of less than thirty and a density substantially less than 0.5 pounds per cubic inch. However, the alloy is body compatible, hemocompatible and highly resilient, with a yield strength (0.2% offset) of at least 350,000 psi, after cold working and age hardening.

Case 26 and core 24 thus cooperate to provide a prosthesis that can be viewed in vivo, and in real time. Of course, the amount of core material in relation to the amount of case material must be sufficient to insure radio-opacity while maintaining the favorable mechanical characteristics of stent 16. It has been found that the area of core 24, taken along a transverse or lateral plane as illustrated in FIG. 4, should be within the range of about ten percent to forty-six percent of the filament lateral cross-sectional area, i.e. the area of the combined case and core.

Tantalum and the Elgiloy alloy are well matched, in that the materials have similar linear coefficients of thermal expansion ($3.6 \times 10^{-6}$ per degree F. and $8.4 \times 10^{-6}$ per degree F., respectively), similar crystalline structures, and annealing temperatures in the range of 1700°–2300°F. Further, there is virtually no tendency for the formation of tritermetallic compounds along the tantalum/Elgiloy alloy triterface.

Platinum and platinum alloys (e.g. platinum-iridium) also are suitable as materials for core 24. The atomic number of platinum is 78, and its density is 0.775 pounds per cubic inch. Its linear attenuation coefficient at 100 MeV is 105 $cm^{-1}$. The linear coefficient of thermal expansion for platinum is about $4.9 \times 10^{-6}$ per degree F.

Thus, as compared to tantalum, platinum is structurally more compatible with the Elgiloy alloy, and more effectively absorbs X-rays. Accordingly, platinum is particularly well suited for use in prostheses formed of small diameter filaments. The primary disadvantage of platinum, with respect to tantalum, is its higher cost.

Further materials suitable for radiopaque core 24 include gold, tungsten, iridium, rhenium, ruthenium, and depleted uranium.

Other materials suitable for case 26 include other cobalt-based alloys, e.g. the Phynox and MP35N brand alloys. Cobalt-chromium and cobalt-chromium-molybdenum orthopedic type alloys also can be employed, as well as alloys of titanium-aluminum-vanadium. The MP35N alloy is widely available, and has a potential for better fatigue strength due to improved manufacturing techniques, particularly as to the vacuum melting process. The titanium-aluminum-vanadium alloys are highly biocompatible, and have more moderate stress/strain responses, i.e. lower elastic moduli.

Figure 8:
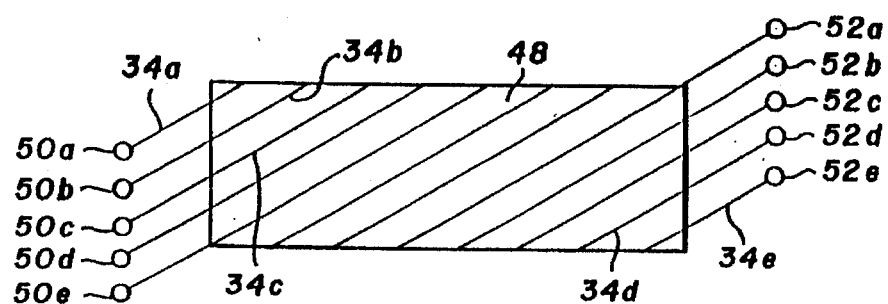
Figure 9:
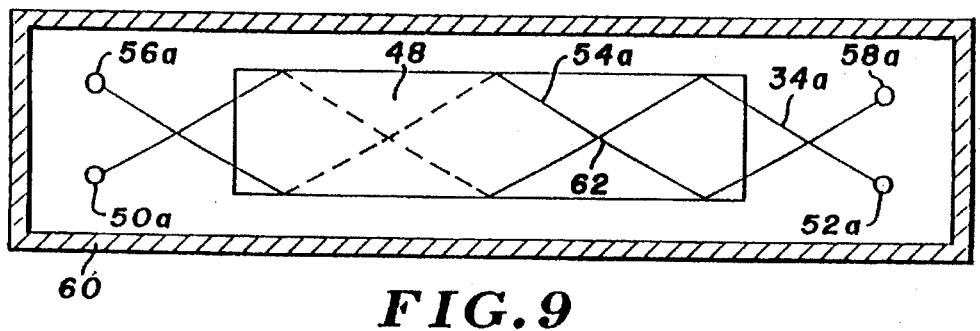

Composite filaments such as filament 18a are manufactured by a drawn filled tubing (DFT) process illustrated schematically in FIGS. 7–9. The DFT process can be performed, for example, by Fort Wayne Metals Research Products corporation of Ft. Wayne, Ind. The process begins with insertion of a solid cylinder or wire 28 of the core material into a central opening 30 of a tube 32 of the case material. Core wire 28 and tubing 32 are substantially uniform in transverse or lateral sections, i.e. sections taken perpendicular to the longitudinal or axial dimension. For example, tube 32 can have an outer diameter d1 of about 0.102 inch (2.6 mm) and an inner diameter d2 (diameter of opening 30) of about 0.056 inches (1.42 mm). Core or wire 28 has an outer diameter d3 slightly less than the tube inner diameter, e.g. 0.046 inches (1.17 mm). In general, the wire outer diameter is sufficiently close to the tubing inner diameter to insure that core or wire 28, upon being inserted into opening 30, is substantially radially centered within the tubing. At the same time, the interior tubing diameter must exceed the core outside diameter sufficiently to facilitate insertion of the wire into an extended length of wire and tubing, e.g. at least twenty feet.

The values of the tubing inner diameter and the core outer diameter vary with the materials involved. For example, platinum as compared to tantalum has a smoother exterior finish when formed into the elongate wire or core. As a result, the outer diameter of a platinum wire can more closely approximate the inner diameter of the tube. Thus it is to be appreciated that the optimum diameter values vary with the materials involved, and the expected length of the, composite filament.

In any event, insertion of the core into the tube forms a composite filament 34, which then is directed through a series of alternating cold-working and annealing steps, as indicated schematically in FIG. 6. More particularly, composite filament 34 is drawn through three dies, indicated at 36, 38, and 40, respectively. In each of the dies, composite filament 34 is cold-worked in radial compression, causing the case tube 32 and the tantalum core wire 28 to cold flow in a manner that elongates the filament while reducing its diameter. Initially, case tube 32 is elongated and radially reduced to a greater extent than core wire 28, due to the minute radial gap that allowed the insertion of the core into the tube. However, the radial gap is closed rapidly as the filament is drawn through die 36, with subsequent pressure within die 36 and the remaining dies cold-working both the core and case together as if they were a single, solid filament. In fact, upon closure of the radial gap, the cold-working within all dies forms a pressure weld along the entire interface of the core and case, to form a bond between the core and case material.

As composite filament 34 is drawn through each die, the cold-working induces strain hardening and other stresses within the filament. Accordingly, respective heating stage is provided, i.e. furnace 42. At each annealing stage, composite filament 34 is heated to a temperature in the range of from about 1700° to about 230° F., or more preferably 1950°–2150° F. At each annealing stage, substantially all of the induced stresses are removed from the case and core, to permit further cold-working. Each annealing step is accomplished in a brief time, e.g. in as few as one to fifteen seconds at annealing temperature, depending on the size of composite filament 34.

While FIG. 6 illustrates one cold-working stage and annealing stage, it is to be understood that the appropriate number of stages is selected in accordance with the final filament size, the desired degree of cross-sectional area reduction during the final cold-working stage, and the initial filament size prior to cold-working. In connection with composite filament 34, a reduction of lateral cross-sectional area in the range of about forty percent to eighty percent is preferred, and a range of about fifty-five percent to sixty-five percent is highly preferred.

The successive cold-working and annealing steps give rise to the need for matching the core and case materials, particularly as to their coefficients of thermal expansion, elastic moduli in tension, annealing temperature ranges, total elongation capacities, and also as to their crystalline structure. A good match of elastic moduli, elongation, and thermal expansion coefficients minimizes the tendency for any ruptures or discontinuities along the core/case interface as the composite filament is processed. Crystalline structures should be considered in matching core and case materials. The Elgiloy alloy, and other-materials used to form case tube 32, commonly experience a transformation between the cold-working and aging steps, from a face centered cubic crystalline structure to a hexagonal close packed crystalline structure. The Elgiloy alloy experiences shrinkage as it undergoes this transformation. Accordingly, the core material must either experience a similar reduction, or be sufficiently ductile to accommodate reduction of the case.

There is no annealing after the final cold, working stage. At this point, composite filament 34 is formed into the shape intended for the device incorporating the filament. In FIG. 8, several filaments or strands 34a–e are helically wound about a cylindrical form 48 and held in place at their opposite ends by sets of bobbins 50a–e and 52a–e. Strands 34a–e can be individually processed, or individual segments of a single annealed and cold-worked composite filament, cut after the final cold-working stage. In either event, the filaments cooperate to form one of the two oppositely directed sets of spaced apart and parallel filaments that form a device such as stent 16. While only one set of filaments is shown, it is to be understood that a corresponding group of filaments, helically wound and intertwined about form 48 in the opposite direction, are supported by corresponding bobbins at the opposite filament ends.

A useful prosthesis depends, in part, upon correctly supporting the filaments. The filaments are maintained in tension, and it is important to select the appropriate tensile force and apply the tensile force uniformly to all filaments. Insufficient tensile force may allow wire cast or lift effects to cause the individual filaments to depart from their helical configuration when released from the bobbins, and the braided structure of the stent may unravel.

FIG. 9 illustrates two filaments 34a and 54a, one from each of the oppositely wound filament sets, supported by respective bobbins 50a/52a and 56a/58a in a furnace 60 for age hardening in a vacuum or protective atmosphere. Age hardening is accomplished at temperatures substantially lower than annealing, e.g. in the range of about 700°–1200° F., more preferably 900°–1022° F. The filaments overlie one another to form several intersections, one of which is indicated at 62. When the filaments are properly tensioned, slight impressions are formed in the overlying filament at each intersection. These impressions, or saddles, tend to positionally lock the filaments relative to one another at the intersections, maintaining the prosthesis configuration without the need for welding or other bonding of filaments at their intersections.

While only two oppositely directed filaments are illustrated as a matter of convenience, it is to be appreciated that the age hardening stage is performed after the winding and tensioning of all filaments, i.e. both oppositely directed sets. Accordingly, during age hardening, the filaments are locked relative to one another at multiple intersections. The preferred time for age hardening is about 1–5 hours. This age hardening step is critical to forming a satisfactory self-expanding prosthesis, as it substantially enhances elasticity, yield strength, and tensile strength. Typically, the elastic modulus is increased by at least 10% and the yield strength (0.2% offset) and tensile strength are each increased by at least 20%.

As an alternative to the process just explained, a substantially larger and shorter composite filament 64 (e.g. six inches long with a diameter of approximately ten cm) can be subjected to a series of elongation/diameter reduction steps. FIG. 10 schematically illustrates two swaging dies 66 and 68, which may be used in the course of a hot working billet reduction process. Of course, any appropriate number of swaging dies may be employed. Alternatively, the diameter reduction can be accomplished by extrusion/pulltrusion at each stage. When a sufficient number of swaging steps have reduced the composite structure diameter to about 6 millimeters (0.25 inches). The composite structure or filament can be further processed by drawing it through dies and annealing, as illustrated in FIG. 6 for the previously discussed process. As before, the composite filament is ready for selective shaping and age hardening after the final cold-working stage.

As compared to the process depicted in FIGS. 5–7, the swaging or pulltrusion approach involves substantially increased hot and cold-working of the composite structure or filament, and the initial assembling of the core into the case or shell tubing is easier. Given the much larger initial composite structure size, the structure is subjected to annealing temperatures for a substantially longer time, e.g. half an hour to an hour, as opposed to the one to fifteen second anneal times associated with the process depicted in FIG. 6. Consequently, particular care must be taken to avoid combinations of core and case materials with tendencies for intermetallic formation along the core/case interface. Further, the required hot working of the larger billet may not afford the same degree of metallurgical grain refinement.

In general, the preferred composite filaments have: (1) sufficient radio-opacity to permit in vivo viewing; (2) the preferred mechanical properties; and (3) a sufficiently low cost. The interrelationship of these factors requires that all three be taken into account in determining filament size, relationship of core 24 to case 26 as to size, and materials selected for the core and case.

More particularly, core 24 should be at least about 0.0015 inches in diameter, if a stent constructed of such filament is to be visible using conventional radiographic imaging equipment. At the same time, structural requirements (particularly elasticity for a self-expanding stent) require a minimum ratio of casing material with respect to core material. Thus, the visibility requirement effectively imposes a minimum diameter upon case 26 as well as core 24. Of course, appropriate selection of core and casing materials can reduce the required minimum diameters. However, potential substitute materials should be considered in view of their impact on cost—not only the material cost per se, but also as to the impact of such substitution on fabrication costs.

Several composite filament structures are particularly preferred in terms of meeting the above requirements. In the first of these structures, the core material is tantalum, and the casing is constructed of the Elgiloy brand cobalt-based alloy. The maximum outer diameter of the composite filament is about 0.150 mm, or about 0.006 inches. Elgiloy filaments of this diameter or larger may be sufficiently radiopaque without a core of tantalum or other more radiopaque material. However, even at such diameters, radio-opacity is improved with a tantalum core, and likewise with a core of a tantalum-based alloy, platinum, platinum-based alloy, tungsten, a tungsten-based alloy or combination of these constituents.

It has been found that the preferred core size, relative to the composite fiber size, varies with the filament diameter. In particular, for larger filament (diameters of 0.10–0.15 mm or 0.004–0.006 inches), sufficient radio-opacity is realized when the cross-sectional area of core 24 is about one-fourth of the cross-sectional are of the entire fiber. For smaller filaments (e.g., 0.07–0.10 mm or 0.00276–0.0039 inches such as the type often used in stents for coronary applications), the core should contribute at least about one-third of the cross-sectional area of the composite filament. Increasing the core percentage above about 33% of the filament cross-sectional area undesirably affects wire mechanical properties and stent elasticity, reducing the ability of a stent constructed of the filament to fully self-expand after its release from a delivery device. Composite filaments of this structure have core diameters in the range of 0.037–0.05 mm (0.0015–0.002 inches), with filament diameters up to about 0.135 mm or about 0.0055 inches.

In a second filament structure, the core is formed of a platinum-10% nickel alloy, i.e. 90% platinum and 10% nickel by weight. While the preferred proportion of nickel is 10%, satisfactory results can be obtained with nickel ranging from about 5% to about 15% of the alloy. The case is constructed of the Elgiloy alloy. The platinum-nickel alloy, as compared to pure tantalum, has superior radiographic and structural properties. More particularly, the alloy has a greater density, combined with a higher atomic number factor (z) for a 10–20% improvement in radio-opacity. Further as compared to tantalum, the alloy is more resistant to fatigue and thus better withstands processes for fabricating stents and other devices. Because of its superior mechanical properties, a corse formed of a platinum-nickel alloy can constitute up to about 40% of the total filament cross-sectional area. Consequently the alloy is particularly well suited for constructing extremely fine filaments. This structure of composite filament is suitable for constructing stents having diameters (unstressed) in the range of about 3.5–6 mm.

As to all composite filament structures, purity of the elements and alloys is important. Accordingly, high purity production techniques, e.g. custom melting (triple melting techniques and electron beam refining) are recommended to provide high purity Elgiloy alloy seamless tubing.

A third filament structure involves an Elgiloy case and a core formed of a tantalum-10% tungsten alloy, although the percentage of tungsten can range from about 5% to about 20%. The tantalum/tungsten alloy is superior to tantalum in terms of mechanical strength and visibility, and costs less than the platinum-nickel alloy.

According to a fourth filament structure, case 26 is formed of the Elgiloy alloy, and core 24 is formed of a platinum-20 to 30% iridium alloy. The platinum-iridium alloy can include from about 5 to about 50% iridium. As compared to the platinum-nickel alloy, the platinum-iridium alloy may exhibit less resistance to fatigue. This is due in part to segregation which may occur during cooling of an alloy containing 30% (by weight) or more iridium, due to the relatively high melting point of iridium. Also, hot working may be required if the alloy contains more than 25% iridium, thereby making final cold reduction of the composite difficult.

A fifth filament structure employs an Eligiloy alloy case and a core of a platinum-tungsten alloy having tungsten in the range of about 5–15%, and more preferably 8%. The radio-opacity of this alloy is superior to the platinum-nickel alloy and it retains the favorable mechanical characteristics.

In a sixth filament structure, casing 26 is constructed of a titanium-based alloy. More particularly, the alloy can be an alloy known as "grade 10" or "Beta 3" alloy, containing titanium along with molybdenum at 11.5%, zirconium at 6%, and tin at 4.5%. Alternatively, the titanium-based alloy can include about 13% niobium, and about 13% zirconium. Core 24 can be formed of tantalum. More preferably, the core is formed of the platinum-10% nickel alloy. In this event, a barrier of tantalum should be formed between the core and case, as is discussed in connection with FIGS. 12 and 13.

The titanium-based alloy case is advantageous, particularly to patients exhibiting sensitivity to the nickel in the Elgiloy alloy, and may further be beneficial since it contains neither cobalt nor chrome. Also, because of the lower modulus of elasticity of the titanium-based alloy (as compared to Elgiloy), stents or other devices using the titanium-based alloy exhibit a more moderate elastic response upon release from a deployment catheter or other device. This may tend to reduce vascular neointimal hyperplasia and consequent restenosis.

Conversely, the lower elastic modulus results in a less favorable matching of the case and core as to elasticity. In filaments utilizing the titanium-based alloy case, the proportion of core material to case material must be reduced. As a result, this construction is suitable for filaments having diameters in the range of about 0.10–0.30 mm.

Finally, according to a seventh filament structure, core 24 is constructed of a tungsten-based alloy including rhenium at 5–40 weight percent. More preferably, the alloy includes rhenium at about 25 percent by weight.

Further preferred materials for core 24 include alloys of about 85–95 weight percent platinum and about 5–15 weight percent nickel; alloys including about 50–95 weight percent platinum and about 5–50 weight percent iridium; alloys including at least 80 weight percent tantalum and at most 20 weight percent tungsten; and alloys including at least 60 weight percent tungsten and at most 40 weight percent rhenium. Further suitable case materials are alloys including about 30–55 weight percent cobalt, 15–25 weight percent chromium, up to 40 weight percent nickel, 5–15 weight percent molybdenum, up to 5 weight percent manganese, and up to 25 weight percent iron. Preferably the material should have a yield strength of at least 150,000 psi (0.2% offset). While less preferred, the case material can have a yield strength of at least 100,000 psi (0.2% offset).

FIG. 11 is an end elevation of a composite filament 74 including a central core 76 of a structural material such as the Elgiloy alloy, surrounded by a radiopaque case 78, thus reversing the respective functions of the core and case as compared to composite filament 34. Composite filament 74, as compared to filament 34, presents a larger and less refractive radiopaque profile for a given composite filament diameter. Composite filament 74, however, is more difficult to manufacture than filaments that employ the structural material as the case.

FIGS. 12 and 13 show a further alternative composite filament 80, consisting of a central radiopaque core 82, an outer annular structural case 84, and an intermediate annular layer 86 between the core and the case. Intermediate layer 86 provides a barrier between the core and case, and is particularly useful in composite filaments employing core and case materials that would be incompatible if contiguous, e.g. due to a tendency to form intermetallics. Materials suitable for barrier layer 86 include tantalum, niobium and platinum. In particular, the barrier layer can be formed of any one of these elements or a combination of more than one of them. As suggested by FIG. 12, the core, barrier layer and case can be provided as a cylinder and two tubes, inserted into one another for manufacture of the composite filament as explained above.

FIG. 14 illustrates another alternative embodiment composite filament 88 having a central radiopaque core 90, a structural case 92, and a relatively thin annular outer cover layer 94. Composite filament 88 is particularly useful when the selected mechanical structure lacks satisfactory biocompatibility, hemocompatibility, or both. Suitable materials for cover layer 94 include tantalum, platinum, iridium, niobium, titanium and stainless steel. The composite filament can be manufactured as explained above, beginning with insertion of the radiopaque core into the structural case, and in turn, inserting the case into a tube formed of the cover material. Alternatively, cover layer 94 can be applied by a vacuum deposition process, as a thin layer (e.g. from ten to a few hundred microns) is all that is required.

The following examples illustrate formation of composite filaments according to the above-disclosed processes.

EXAMPLE 1

An elongate tantalum core having a diameter of 0.46 inches (1.17 mm) was assembled into an Elgiloy alloy case having an outer diameter of 0.102 inches (2.6 mm) and an inner diameter of 0.056 inches (1.42 mm). Accordingly, the lateral cross-sectional area of the tantalum core was about 25% of the composite filament lateral cross-sectional area. Composite filaments so constructed were subjected to 5–6 alternating stages of cold-working and annealing, to reduce the outer diameters of the composite filaments to values within the range of 0.004–0.0067 inches. The tantalum core diameters were reduced to values in the range of 0.002–0.0034 inches. The composite filaments were formed into a stent suitable for biliary applications, and age hardened for up to five hours, at temperatures in the range of 900°–1000° F.

EXAMPLE 2

Elongate cores of a platinum iridium alloy (20% by weight iridium), with initial core outer diameters of 0.088 inches, were inserted into annular Elgiloy cases with outer diameters of 0.144 inches and inside diameters of 0.098 inches. The resulting composite filaments were processed through about six cold-working and annealing cycles as in the first example, to reduce the outer filament diameter to values within the range of 0.00276 inches–0.0039 inches, and reducing the core outer diameter to values in the range of 0.0018–0.0026 inches. The core thus constituted 43% of the filament lateral cross-sectional area. The resulting filaments were formed into a small vascular stent, and age hardened for approximately three hours.

EXAMPLE 3

Composite filaments were constructed and processed substantially as in example 2, except that the core was formed of a platinum nickel alloy, with nickel 10% by weight.

EXAMPLE 4

The composite filaments were constructed and processed as in examples 2 and 3, except that the core was formed of tantalum, and the case was formed of MP35N alloy, and the cold-working stages reduced the filament outer diameter to values in the range of 0.00276–0.0047 inches.

In the case of all examples above, the resulting stents exhibited satisfactory elasticity and were readily fluoroscopically imaged in real time.

In other embodiments, the device has an additional layer covering the case. Possible materials for the additional layer include tantalum, gold, titanium, and platinum. The additional layer preferably has a thickness in the range of about 0.005–5.0 microns, and can be applied by methods such as thin clad overlay co-drawing, electrochemical deposition of the metal after fabrication of the composite filament, ion implantation (such as physical vapor deposition and ion beam deposition), and sputter coating. Preferably the additional layer is a metal having an electronegative surface such as tantalum.

Each of the above described composite filaments combines the desired structural stability and resiliency, with radio-opacity that allows in vivo imaging of the device composed of the filaments, during deployment and after device fixation. This result is achieved by a drawn filled tubing process that cold works a central core and its surrounding case, to positively bond the core and case together such that the composite filament behaves as a continuous, solid structure. Performance of the filament and resulting device is further enhanced by a selective matching of the core and case materials, as to linear thermal expansion coefficient, annealing temperature, moduli of elasticity, and crystalline structure.

What is claimed is:

1. A body compatible device comprising:
  an elongate filament substantially uniform in lateral cross-section over a length or the filament comprising an elongate core and an elongate case surrounding the core substantially over said length; and
  a barrier layer surrounding the core and disposed between the core and the case substantially over said length;
  wherein the case is constructed of a case material having a yield strength of at least 100,000 psi at 0.2 percent offset, and the core is constructed of a core material from the group consisting of: tantalum, a tantalum-based alloy, platinum, a platinum-based alloy, tungsten, a tungsten-based alloy, and combinations thereof.

2. The device of claim 1 wherein:
  said barrier layer is constructed of a material from the group consisting of: tantalum, niobium, platinum, and combinations thereof.

3. The device of claim 1 wherein:
  said core material comprises said tantalum-based alloy, and a tantalum-based alloy comprises tungsten at about 5–20 percent by weight.

4. The device of claim 1 wherein:
  said case material comprises a cobalt-based alloy.

5. The device of claim 1 wherein:
  said case material comprises a titanium-based alloy.

6. The device of claim 1 wherein:
  said core material comprises said platinum-based alloy, and the platinum alloy consists essentially of platinum and a material from the consisting of group: nickel at from 5–15 percent; iridium at from 5–50 percent; and tungsten at about 5–15 percent.

7. The device of claim 1 wherein:
  said core material comprises tungsten-based alloy, and the tungsten-based alloy comprises rhenium at 5–40 percent, by weight.

8. A body compatible device including a plurality of elongate filaments as defined in claim 1, wherein:
  said elongate filaments are helically wound in at least two oppositely directed sets of spaced apart filaments, with said sets of filaments interwoven with one another in a braided configuration.

9. A body compatible device comprising:
  an elongate filament substantially uniform in lateral cross-section over a length of the filament comprising an elongate core and an elongate case surrounding the core substantially over said length; and
  a barrier layer surrounding the core and disposed between the core and case substantially over said length;
  wherein the core is constructed of a core material having a linear attenuation coefficient of at least 25 $cm^{-1}$ at 100 KeV, and the case is constructed of a case material, said core material being more ductile and more radiopaque than the case material, and wherein the case material comprises a titanium-based alloy.

10. The device of claim 9 wherein:
  said barrier layer is formed of a material from the group consisting of: tantalum, niobium, platinum, and combinations thereof.

11. The device of claim 9 wherein:
  said titanium-based alloy includes niobium at about 10–15 percent, and zirconium at about 10–15 percent, by weight.

12. The device of claim 11 wherein:
  said titanium-based alloy further includes molybdenum and tin.

13. The device of claim 9 wherein:
  said core material consists essentially of a material from the group consisting of: tantalum, a tantalum-based alloy, a platinum-based alloy, and combinations thereof.

14. The device of claim 13 wherein:
  said core material consists essentially of said platinum-based alloy.

15. A resilient, body implantible prosthesis including a plurality of elongate filaments as defined in claim 9, wherein:

said elongate filaments are helically wound in at least two oppositely directed sets of spaced apart filaments with said sets of filaments interwoven with one another in a braided configuration.

16. A body compatible device comprising:

an elongate filament substantially uniform in lateral cross-section over a length of the filament comprising an elongate core and an elongate case surrounding the core substantially over said length; and a barrier layer surrounding the core and disposed between the core and the case substantially over said length;

wherein the core is formed of a core material comprising an essentially unalloyed tantalum and the case is formed of a case material comprising about 30–55 weight percent cobalt, about 15–25 weight percent chromium, about 0–40 weight percent nickel, about 5–15 weight percent molybdenum, about 0–5 weight percent manganese, and about 0–25 weight percent iron.

17. The device of claim 16 wherein:

said barrier layer is formed of a material from the group consisting of: tantalum, niobium, and platinum.

18. A resilient, body implantible prosthesis including a plurality of elongate filaments as defined in claim 16, wherein:

said elongate filaments are helically wound in at least two oppositely directed sets of spaced apart filaments, with said sets of filaments interwoven with one another in a braided configuration.

19. A body compatible device comprising:

an elongate filament substantially uniform in lateral cross-section over a length of the filament comprising an elongate core and an elongate case surrounding the core substantially over said length; and a barrier layer surrounding the core and disposed between the core and the case substantially over said length;

wherein the core material comprises about 85–95 weight percent platinum and about 5–15 weight percent nickel, and the case is formed of a case material comprising about 30–55 weight percent cobalt, about 15–25 weight percent chromium, about 0–40 weight percent nickel, about 5–15 weight percent molybdenum, about 0–5 weight percent manganese, and about 0–25 weight percent iron.

20. The device of claim 19 wherein:

said barrier layer is formed of a material from the group consisting of: tantalum, niobium, platinum, and combinations thereof.

21. The device of claim 19 wherein:

said core material comprises about 10 percent nickel.

22. A resilient, body implantible prosthesis including a plurality of elongate filaments as defined in claim 19, wherein:

said elongate filaments are helically wound in at least two oppositely directed sets of spaced apart filaments, with said sets of filaments interwoven with one another in a braided configuration.

\* \* \* \* \*